United States Patent [19]

Ochiai et al.

[11] 4,018,230
[45] Apr. 19, 1977

[54] CERVICAL DILATOR

[76] Inventors: Kazuo Ochiai, No. 35-7, 1-chome, Nishiikebukuro, Toshima, Tokyo; Masayasu Mizutani, No. 7-3-19, Koyama, Shinagawa, Tokyo, both of Japan

[22] Filed: Apr. 2, 1975

[21] Appl. No.: 564,346

[30] Foreign Application Priority Data

Apr. 4, 1974  Japan .......................... 49-038386

[52] U.S. Cl. ............................................... 128/344
[51] Int. Cl.² ........................................ A61M 29/00
[58] Field of Search .................................... 128/344

[56] References Cited

UNITED STATES PATENTS

| | | | |
|---|---|---|---|
| 157,343 | 12/1874 | Molesworth | 128/344 |
| 899,477 | 9/1908 | Williams | 128/344 |
| 2,701,559 | 2/1955 | Cooper | 128/344 X |
| 3,626,949 | 12/1971 | Shute | 128/344 |

FOREIGN PATENTS OR APPLICATIONS

| | | | |
|---|---|---|---|
| 71,570 | 1/1893 | Germany | 128/344 |
| 334,404 | 1/1936 | Italy | 128/344 |
| 493,784 | 10/1938 | United Kingdom | 128/344 |

*Primary Examiner*—Channing L. Pace
*Attorney, Agent, or Firm*—Weiser, Stapler & Spivak

[57] ABSTRACT

A cervical dilator is formed of a mushroom shaped elastic sack having inelastic members embedded therein configured to maintain the general shape and limit the size of the sack during expansion under internal pressure.

The dilator is inserted with the head portion folded and fluid is introduced to unfold it and expand it.

12 Claims, 17 Drawing Figures

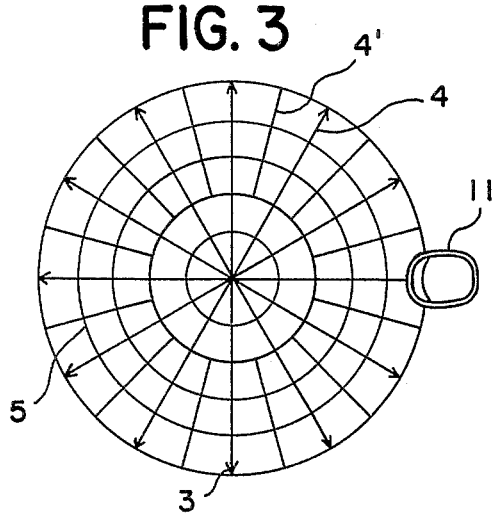
FIG. 3
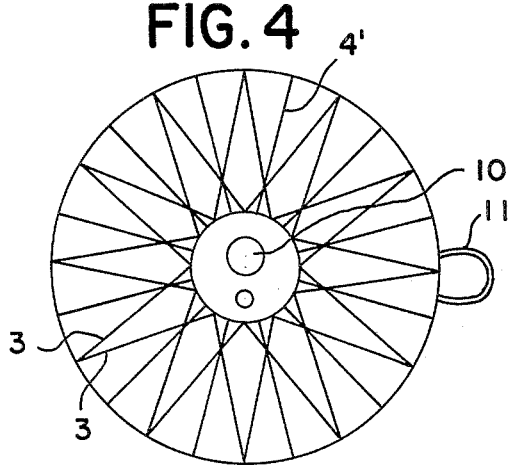
FIG. 4
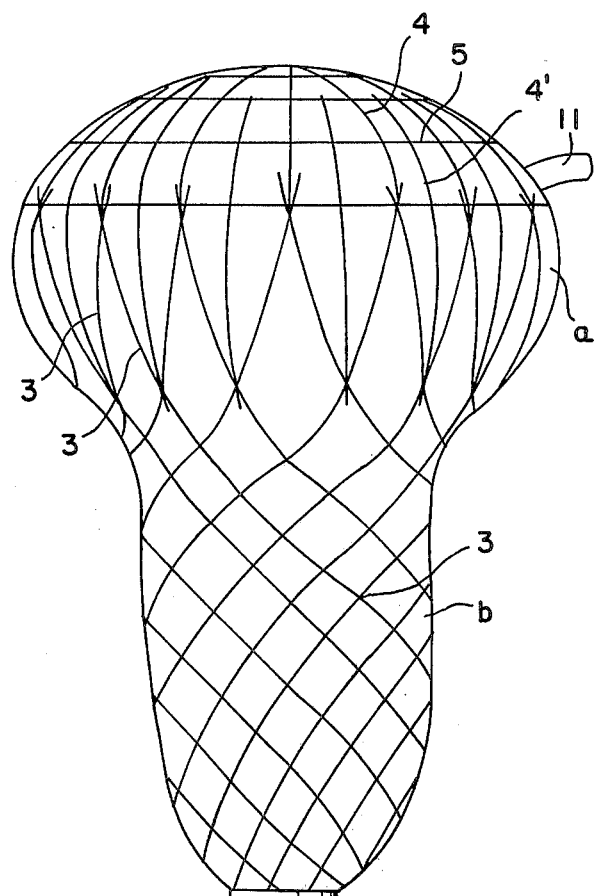
FIG. 5
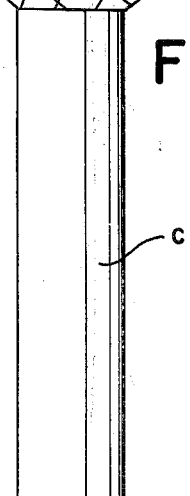

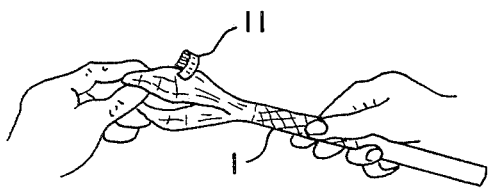
FIG. 6A
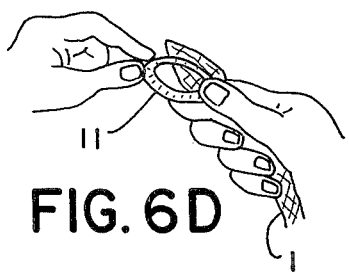
FIG. 6D
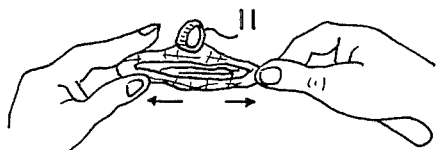
FIG. 6B
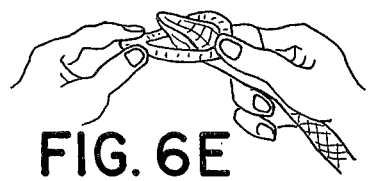
FIG. 6E
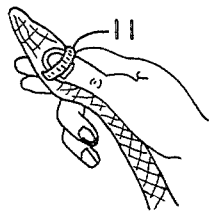
FIG. 6C
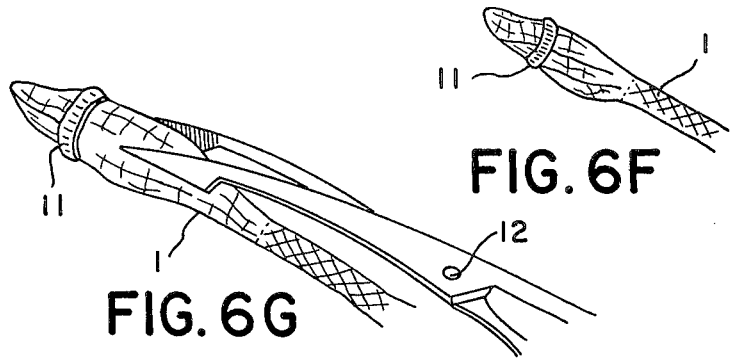
FIG. 6F
FIG. 6G
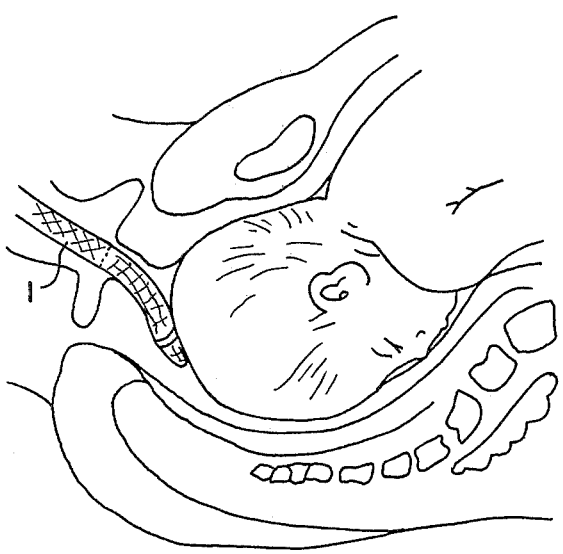
FIG. 7
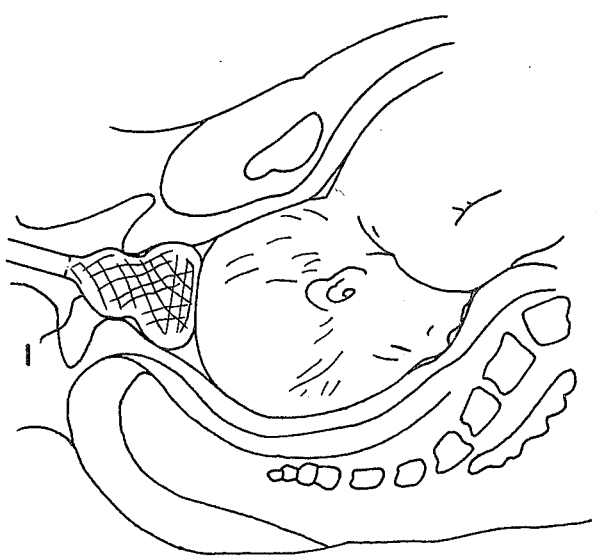
FIG. 8

| | | |
|---|---|---|
| 100 cc | 0.1 mm Hg |  |
| 200 cc | 0.2 mm Hg |  |
| 300 cc | 0.3 mm Hg |  |
| 400 cc | 0.4 mm Hg |  |
| 500 cc | 0.5 mm Hg |  |

CERVICAL DILATOR

BACKGROUND OF THE INVENTION

This invention relates to a cervical dilator.

In the case of overdue delivery owing to an insufficient opening of the cervix which may be caused by insufficient rotation of the fetus' head or by abnormal delivery because of the fetus' size, steps must be taken to effect a delivery which will not injure the mother's body or the fetus by dilating the cervix artificially.

The present methods of dilating the cervix are generally as follows: Hegar's dilator, Bossi's dilator colpeurynter, half colpeurynter, folding type of colpeurynter, metreurynter, dilator of metal spring type, Bougie, and the method of inserting gauze into the cervix.

These methods, however, have little effect in dilating the cervix and are difficult in use. Accordingly, injury to the mother's body and to the fetus often occur.

For example, Bossi's dilator, and the dilator of the metal spring type are apt to injure the cervix of the mother's body. The structure of the colpeurynter and metreurynter types cause difficulty in inserting them into the uterus. In the use of these instruments, the position of the fetus is apt to be changed suddenly from the occipital position to the sacral position, thereby pressing against the fetus' head. Further, in the use of the colpeurynter, it is usual to expand the device by pouring water into it after it is inserted into the uterus and then to pull it by weight at the end of the tube. In this procedure, however, often the device slips off outside of the uterus and dilation of the cervix cannot then be obtained.

SUMMARY OF THE INVENTION

This invention relates to a cervical dilator which is used to perform a safe delivery by dilating the cervix either swiftly or slowly as in the case of an over term delivery due to incomplete opening of the uterus in the delivery process which may be caused by weak labor, incomplete rotation of the fetus' head, over term pregnancy, early rupture, early delivery due to the irregular heartbeat of the fetus, or artificial abortion in midterm. This invention can also be applied in veterinary medicine to animals such as cows, pigs and similar animals.

The explanation of drawings in according with the composition of this invention is as follows:

BRIEF DESCRIPTION OF THE DRAWINGS

FIG. 3 is a top plan view looking from the top of FIG. 1;

FIG. 4 is a bottom plan view looking from the bottom of FIG. 1;

FIG. 5 is a side elevational view similar to FIG. 1 showing the expanded form when the cervix is dilated;

FIGS. 6A, 6B, 6C, 6D, 6E, 6F, 6G are isometric views showing preparatory steps prior to using the device;

FIGS. 7 and 8 show the device in use;

DESCRIPTION OF THE PREFERRED EMBODIMENT OF THE INVENTION

Figures 1, 2:
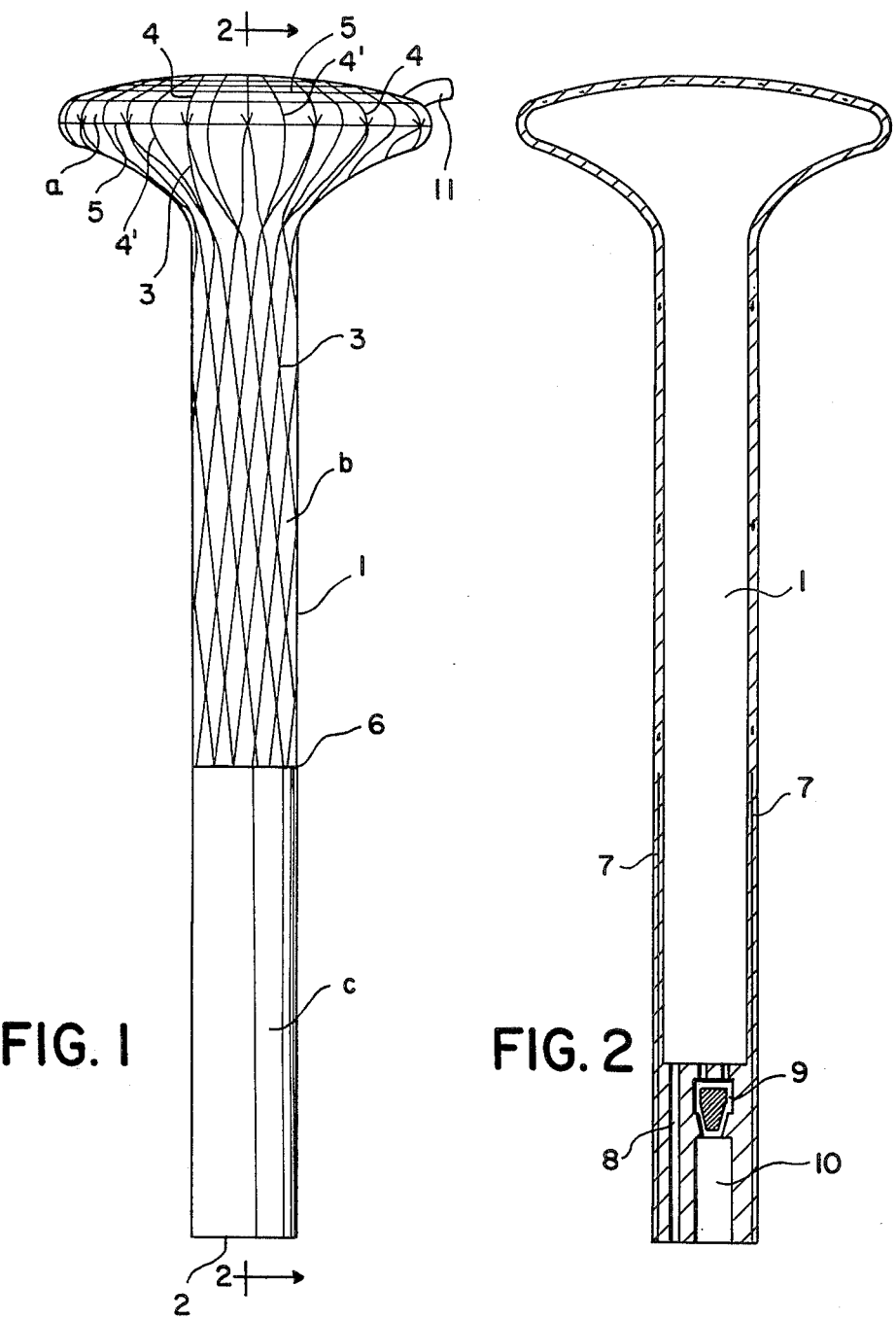
FIG. 1 is a front elevational view of a cervical dilator in accordance with the present invention.
FIG. 2 is a cross sectional view taken along Line 2—2 of FIG. 1, looking in the direction of the arrows.

The form of the main body 1 in accordance with this invention is in the general configuration of a mushroom as illustrated in FIG. 1 having a flat head $a$ and a hollow cylindrical stem $b$. The main body 1 is fabricated of thin rubber or other resilient material into which nets and cloths may be laminated or otherwise affixed for strengthening and shaping purposes as hereinafter more fully set forth. The main body 1 is divided generally into three sections, namely a head $a$, a stem $b$ and a root section $c$. The head $a$ terminates in a flat, disc-like surface.

Figure 11:
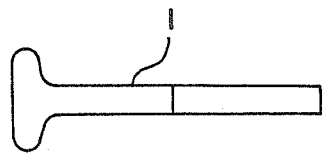
FIG. 11 is a schematic view showing the change of form of the device under various operating pressures and capacities.
Figure 11:
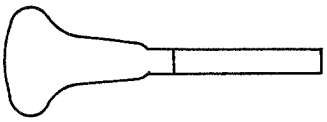
Figure 11:
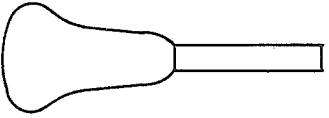
Figure 11:
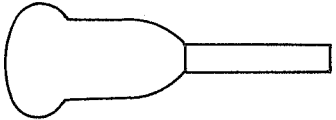
Figure 11:
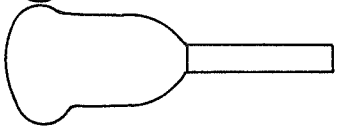

The body 1 may be expanded in a manner similar to that of a rubber tube when pressurized at the inlet 2 of the root section $c$. Nets and cloths are preferably laminated to or otherwise affixed to the rubber material comprising the body 1 to shape the device to an expected form when pressurized. FIG. 11 shows various shapes which the cervical dilator may assume in accordance with this invention when it is pressurized with a hydraulic pump or otherwise expanded.

A method of affixing the nets in the rubber materials at the time of formation of main body is described as follows.

The nets 3 which may be of rhombic or diamond shape as shown in FIG. 1 are allowed to attain each end of their strings to loop strings 5 which lie along the outer circumstance of head $a$. The nets extend through the back of head $a$ from the surface of stem $b$. Said strings extend the length of the stem $b$ from the end 6 to the head $a$.

The radial nets 4 as shown in FIG. 3 are connected to the and pass side strings 5 passing through the center of head $a$ starting from loop strings 5 which lie around the head $a$. The radial nets 4' as shown in FIG. 3 and FIG. 4, extend to the vicinity of the center of head $a$ starting from the back of head $a$ alternatively with radial nets 4. Each string is arranged to define approximately equal angles therebetween from the center of head $a$.

Many of the loop strings 5 as illustrated in FIG. 3 are concentrically arranged and extend from the center of head $a$ to the outer periphery of the head.

At root section $c$, the cloths 7 are laminated or otherwise affixed to the rubber materials so that said root section $c$ may not be expanded even if pressurized. This part is a composite part with other attachments, and include a pouring tube 10 provided with an air-drain pipe 8 and check valve 9 as shown in FIG. 2.

When said dilator is subjected to hydraulic pressure from a hydraulic pump 13 made of rubber materials (FIG. 9) from pouring tube 10, the root section $c$ is not transformed because of intervention with the cloths 7 in the rubber materials. The stem $b$ and cap $c$ are expanded to a form shown in FIG. 5 because loop strings which form rhombic nets 3 in the back of both $b$ and $c$, are intervened in the rubber materials. The head $a$ holds the original form. The expansion of rubber materials is controlled by the strain of strings because said cap is composed of radial nets 4 and loop strings 5. In FIGS. 3, 4, 5, 11 shows a rubber band attached to said head of cap $a$.

As the result of composition as described above, the dilator of cervix according to this invention can be used as follows. When a cervix of pregnant woman who is weak in travail or has a near scheduled delivery, is opened to one finger width, the external labium of said pregnant woman is cleaned and disinfected with chimerosal exposing the vagina with Cusco speculum. The vagina of the pregnant woman is disinfected. The upper and lower portions are held apart with Museux's forcepts and the O. m. is inserted.

As shown in FIG. 6 hold the stem with the right hand FIG. 6A and stretch the top of the head with the other hand and fold the outer surface to the inside to the shape of a finger like (6 - 2) and stretch the small rubber band 11 around the head (FIG. 6c).

Then, said rubber band is pulled holding the base of the rubber band (FIG. 6D) and brought to the condition shown in FIG. 6E by pulling up the rubber band on the top of this device which is folded to elongated configuration as illustrated in FIG. 6F. Said device is inserted into a lower bottom part of the advanced part of fetus as shown in FIG. 7 holding a dressing forceps 12 (FIG. 6G).

Figure 9:
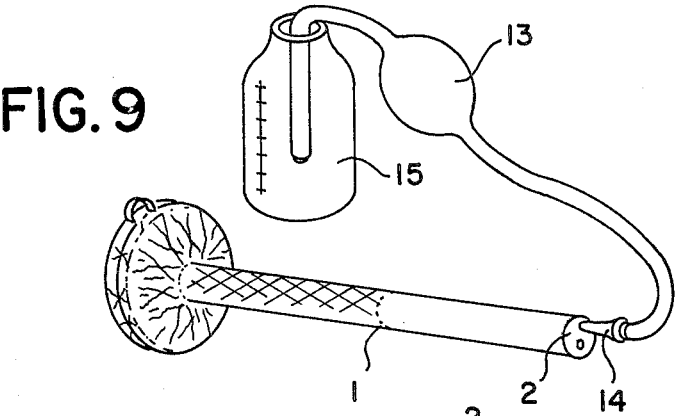
FIG. 9 is an isometric view showing the device assembled with other apparatus prior to use.
Figure 10:
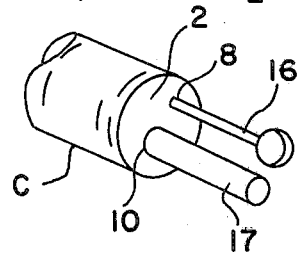
FIG. 10 is an enlarged, perspective view showing details of end connections.

A beak tube 14 of a hydraulic pump 13 is inserted into the pouring tube 10 as shown in FIG. 9 and a conduit at the other end of said hydraulic pump is inserted into distillate 15. Then said pump is compressed to discharge the air and water in the device from air-drain pipe 8 and a cork or stop cork 16 is placed to close the drain pipe.

At this time, the rubber band is spontaneously released allowing to expand the slenderly folded head of this device. Approximately 200 c.c of water is poured into the device by compressing said pump. An operator disconnects the beak tube 14 of the rubber pump after confirming whether the device is inserted properly into the cervix, and allows the patient to return to her patient room, and observes her condition for a while. In case no labor occurs then approximaely even after two hours, another 100 c.c of water is poured using said pump so that total amount of water may be about 300 c.c. to 400 c.c. When the cervix is opened by swelling to the condition as shown in FIG. 8, the delivery is near in accordance with higher labor and abdomen pressure.

This invention is, as described above, simple in insertion of the device into the uterus, and injury to the cervix will not occur because the device is made of soft and thin rubber. Further, as the head part of the device is comparatively flat, the head of the fetus is not pressed and is pushed about 2 cm., as the device is expanded. There is no need to pull the main body like a colpeurynter as the back of stem *b* to cap *a* is expanded slowly and is allowed to dilate the cervix by the hydraulic pressure from the pump. Further more, this device is designed so that it may be expanded slowly by pressure and amount of water as shown in FIG. 11, and condition of device within the cervix may be conceived by the amount of pouring water, and in addition the dilating rate of cervix may also be controlled in accordance with the condition.

Accordingly, this invention is effective as a device for delivery in lowering the fatigue of not only the fetus and mothers's body but also of midwife reducing the delivery time.

We claim:

1. A cervical dilator comprising:
    a sack of elastic material expandable under internal pressure, said sack comprising a shaped head and a stem communicating with the head, said head terminating in flat, generally disc-like surface, and
    a network of interconnected inelastic members embedded in portions of said material,
    said inelastic members being configured to define the shape and limit the size of said sack during expansion under said internal pressure.

2. The dilator of claim 1 wherein said shaped head maintains its flat, disc-like surface in both its expanded and unexpanded condition.

3. The dilator of claim 1, wherein said inelastic members are stringlike and form a first pattern in the stem, a second pattern on the head, said second pattern comprising a plurality of concentric hoop members.

4. The dilator of claim 3, wherein said second pattern comprises a plurality of radially arranged members.

5. The dilator of claim 4, wherein at least some alternate ones of said radial members meet at the center of said head and at least some intermediate ones of said radial members stop at a hoop member.

6. The dilator of claim 1, further comprising an elastic loop attached to the head, said loop being adapted to encircle said head when folded and to constrict it for cervical insertion.

7. The dilator of claim 1, wherein said stem encloses, at its end remote from said head, a pouring tube and check valve for introducing pressurizing fluid into said sac, an air drain and an air drain stop cock.

8. The dilator of claim 1 wherein a portion of said stem furthest from said sack has affixed to said elastic material an inelastic material so configured as to substantially preclude expansion of said portion.

9. A method of cervical dilation utilizing a sack of elastic material having a shaped head portion and a tubular stem portion, said method comprising the steps of:
    folding said head portion lengthwise to reduce its width,
    inserting said sack into the cervix with said head portion folded lengthwise; and
    introducing fluid into said sack through said stem portion to expand said sack within the cervix.

10. The method of claim 9, wherein said expanding includes unfolding said head portion within the cervix.

11. The method of claim 10, wherein said folding includes encircling the folded head with an elastic band to maintain the folded condition and unfolding includes releasing the elastic band from encircling said folded head portion.

12. A cervical dilator which comprises: a series of rhombic nets 3 extending from a stem 6 to a back of a head *a* embedded in rubber materials of a main body 1 which is made of a thin rubber sack, said rubber sack being maintained in an expanded form by the tension of strings composed of radial nets 4 and 4', and interconnected hoop strings 5 at the head when pressurized; cloths 7 affixed to a bottom section *c* of said main body 1 so that said rubber materials of the bottom section may not be expanded with pressure; and an elastic band 11 bonded to the head and being adapted to encircle a portion of the head when longitudinally folded to maintain the folded condition of the head.

* * * * *